US012763214B2

(12) United States Patent
Kim et al.

(10) Patent No.: US 12,763,214 B2
(45) Date of Patent: Oct. 13, 2026

(54) USER TERMINAL AND METHOD FOR MANAGING STATUS THROUGH USER TERMINAL AFTER AUTOMATICALLY INJECTING MEDICATION

(71) Applicant: IPV, Seoul (KR)

(72) Inventors: Jesse J. Kim, Seongnam-si (KR); Inwook Bin, Yongin-si (KR)

(73) Assignee: IPV, Seoul (KR)

( * ) Notice: Subject to any disclaimer, the term of this patent is extended or adjusted under 35 U.S.C. 154(b) by 1345 days.

(21) Appl. No.: 17/596,328

(22) PCT Filed: Jun. 10, 2020

(86) PCT No.: PCT/KR2020/007499
§ 371 (c)(1),
(2) Date: Dec. 7, 2021

(87) PCT Pub. No.: WO2020/251251
PCT Pub. Date: Dec. 17, 2020

(65) Prior Publication Data

US 2022/0230756 A1 Jul. 21, 2022

(30) Foreign Application Priority Data

Jun. 12, 2019 (KR) ........................ 10-2019-0069565

(51) Int. Cl.

| | |
|---|---|
| ***G16H 50/30*** | (2018.01) |
| ***G06Q 20/08*** | (2012.01) |
| ***G08B 21/18*** | (2006.01) |
| ***G16H 20/17*** | (2018.01) |

(52) U.S. Cl.
CPC ........... *G16H 50/30* (2018.01); *G06Q 20/085* (2013.01); *G08B 21/18* (2013.01); *G16H 20/17* (2018.01)

(58) Field of Classification Search
CPC ...... G16H 50/30; G16H 20/17; G06Q 20/085; G08B 21/18
See application file for complete search history.

(56) References Cited

U.S. PATENT DOCUMENTS

| | | | | |
|---|---|---|---|---|
| 9,807,174 | B2 * | 10/2017 | Starr | H04L 67/12 |
| 2011/0021140 | A1 * | 1/2011 | Binier | G06Q 40/08 455/41.1 |
| 2018/0075200 | A1 | 3/2018 | Davis et al. | |

FOREIGN PATENT DOCUMENTS

| | | | |
|---|---|---|---|
| JP | 2018-185857 | A | 11/2018 |
| KR | 10-2001-0109400 | A | 12/2001 |
| KR | 10-2009-0095073 | A | 9/2009 |
| KR | 10-2015-0085445 | A | 7/2015 |
| KR | 10-2016-0007678 | A | 1/2016 |
| KR | 10-1751274 | B1 | 6/2017 |
| KR | 10-2017-0135362 | A | 12/2017 |
| KR | 10-2018-0000068 | A | 1/2018 |
| KR | 10-1886334 | B1 | 8/2018 |

OTHER PUBLICATIONS

International Search Report issued for International Patent Application No. PCT/KR2020/007499, dated Apr. 1, 2021 in 4 pages.
Written Opinion issued for International Patent Application No. PCT/KR2020/007499, dated Apr. 1, 2021 in 5 pages.
Office Action issued in the counterpart Korean Patent Application No. 10-2019-0069565, dated Jun. 30, 2021 in 6 pages.
Korean Notice of Allowance issued in the counterpart Korean Patent Application No. 10-2019-0069565, dated Oct. 30, 2021 in 2 pages.

* cited by examiner

*Primary Examiner* — Jerry Lin
(74) *Attorney, Agent, or Firm* — Knobbe, Martens, Olson & Bear, LLP

(57) ABSTRACT

According to an embodiment, provided is a method of managing a state after automatically injecting medicine, including: installing, by a first user terminal, a drug injection program received from a management server thereon; receiving, by the first user terminal, at least one from usage data of a drug injection device, a drug injection message, a biometric value measurement message, and a device state message from a controller via the drug injection program; receiving, by the first user terminal, an input of a risk alarm setting information from a user and transmitting the risk alarm setting information to the controller; receiving, by the first user terminal, a risk signal corresponding to the risk alarm setting information from the controller; and determining, by the first user terminal, a manager according to the risk signal, and transmitting a risk alarm message to a terminal of the manager according to the risk signal or a risk management center.

7 Claims, 17 Drawing Sheets

USER TERMINAL AND METHOD FOR MANAGING STATUS THROUGH USER TERMINAL AFTER AUTOMATICALLY INJECTING MEDICATION

CROSS-REFERENCE TO RELATED APPLICATIONS

This application is the U.S. National Phase under 35. U.S.C. § 371 of International Application PCT/KR2020/007499, filed Jun. 10, 2020, which claims priority to Korean Patent Application No. 10-2019-0069565, filed Jun. 12, 2019. The disclosures of the above-described applications are hereby incorporated by reference in their entireties.

BACKGROUND

Field

The present disclosure relates to a user terminal and a method of managing a state through the user terminal after automatically injecting medication.

DESCRIPTION OF THE RELATED ART

Diabetes is a metabolic disorder that generates a sign indicating that a blood sugar level exceeds a normal range because of insufficient insulin secretion or abnormal function. Diabetes is a complex disease that possibly affects individual tissues of a human body due to complications such as blindness, renal failure, heart failure, and neuropathy, etc., and the number of diabetic patients is increasing every year.

In the case of diabetes, it is necessary to measure a blood sugar level using a blood sugar meter, and to manage the blood sugar level through appropriate means such as diet, exercise program, insulin injection, oral diabetes medication, etc.

(Patent Document 1) 0001) Patent Publication No. 2009-0095073

SUMMARY OF CERTAIN INVENTIVE ASPECTS

The present disclosure is to provide a user terminal that receives a drug injection message, a biometric value measurement message, and a device state message from a controller connected to a drug injection device and transmits a risk alarm indicating a current state to a manager terminal, and a method of managing the state through the user terminal after automatically injecting medication.

According to an embodiment of the present disclosure, a method of managing a state after automatically injecting medicine includes: installing, by a first user terminal, a drug injection program received from a management server thereon; receiving, by the first user terminal, at least one from usage data of a drug injection device, a drug injection message, a biometric value measurement message, and a device state message from a controller via the drug injection program; receiving, by the first user terminal, an input of a risk alarm setting information from a user and transmitting the risk alarm setting information to the controller; receiving, by the first user terminal, a risk signal corresponding to the risk alarm setting information from the controller; and determining, by the first user terminal, a manager according to the risk signal, and transmitting a risk alarm message to a terminal of the manager according to the risk signal or a risk management center.

According to the embodiment, when the risk signal is received or generated, a chat room including a recipient group registered as a manager of the user is generated, and one-to-one message transmission among participants in the chat room is controlled to be impossible, and the risk alarm message of the user may be shared through the chat room.

The risk alarm message may further include location information and may be implemented to generate an additional alarm at a preset time point.

According to the embodiment, the method may further include: receiving, by the first user terminal, a device state message from the controller and transmitting usage data of the drug injection device to the management server during a drug non-injection time period; receiving, by the first user terminal, a payment link of a usage fee corresponding to the usage data from the management server; and executing, by the first user terminal, the drug injection program on finishing payment and approval of the usage fee corresponding to usage data via the payment link.

According to the embodiment, the method may include: when a blood sugar value corresponds to the risk of hypoglycemia or the risk of hyperglycemia, requesting, to a management server, information on an insulin injection amount for removing the hypoglycemia risk or hyperglycemia risk; and receiving a payment link for disclosing information received from the management server, and when the payment through the payment link is approved, receiving the insulin injection amount information for removing the risk, and transmitting the insulin injection amount information for removing the risk to the controller that is connected thereto in advance. When a risk signal is received or generated, the method may further include determining a recipient group of the risk alarm message according to a risk code of the risky situation and a type of the risk.

According to the embodiment, the method may include: transmitting to the management server an access signal to the drug injection program through a second user terminal that is different from the first user terminal, and executing, by the second user terminal, a user authentication process via user identification information; and when the user authentication process is true, accessing the management server and providing a screen synchronized with the first user terminal.

According to the embodiment, the method may include: registering, by the first user terminal, time zone setting information to the controller by the user; and changing a reception time point of at least one from the drug injection message, the biometric value measurement message, and the device state message from the controller based on the time zone setting information.

A user terminal for managing a state after automatically injecting medicine according to an embodiment of the present disclosure may include: a message receiving unit for receiving at least one from a drug injection message including usage data of a drug injection device, a biometric value measurement message, and a device state message from a controller via a drug injection program installed thereon; an information registration unit for registering risk alarm setting information; a risk signal generation unit for receiving from the controller a risk signal corresponding to the risk alarm setting information that is determined by using at least one from the drug injection message, the biometric value measurement message, and the device state message; and a risk alarm generation unit for determining a manager according to the risk signal, and transmitting a risk alarm message to a terminal of the manager according to the risk signal or a risk management center.

When the occurrence of the risky situation is true, the risk alarm generation unit may generate a chat room including the recipient group registered as the manager of the user, and control one-to-one message transmission among participants in the chat room to be impossible, but share the risk alarm message of the user through the chat room.

According to the embodiment, the user terminal may further include a usage data processing unit that, when an event in which the use of the drug injection program is restricted occurs, transmits usage data to the management server during the drug non-injection time at a request of the management server, receives a payment link of a usage fee corresponding to the usage data from the management server, and executes the drug injection program when payment and approval of the usage fee corresponding to user data are finished through the payment link.

According to the embodiment, when a blood sugar value corresponds to the risk of hypoglycemia or the risk of hyperglycemia, a reference processing unit may request, to a management server, information on an insulin injection amount for removing the hypoglycemia risk or hyperglycemia risk, and may receive from the management server a payment link for information disclosure, and when the payment through the payment link is approved, the reference processing unit may receive the insulin injection amount information for removing the risk, and may transmit the insulin injection amount information for removing the risk to the controller that is connected thereto in advance.

According to the embodiment, when the risk signal is received or generated, the risk alarm generation unit may determine a recipient group of a risk alarm message according to a risk code of the risky situation and a type of the risk.

The information registration unit may register time zone setting information to the controller by the user, and based on the time zone setting information, may change the reception time point of at least one from the drug injection message, the biometric value measurement message, and the device state message from the controller.

A computer program according to an embodiment of the present disclosure may be stored in a medium to execute any one of the methods according to the embodiment of the present disclosure by using a computer.

In addition, another method for implementing the present disclosure, another system, and a computer-readable recording medium for recording a computer program for executing the method are further provided.

Other aspects, features and advantages of the disclosure will become better understood through the accompanying drawings, the claims and the detailed description.

According to the present disclosure, a drug injection message, a biometric value measurement message, and a device state message may be received from a controller connected to a drug injection device and a danger alarm indicating a current state may be transmitted to a manager terminal. When there is no confirmation message with respect to the danger alarm, location information of a user may be transmitted to the manager terminal.

DETAILED DESCRIPTION OF CERTAIN ILLUSTRATIVE EMBODIMENTS

Figure 1:
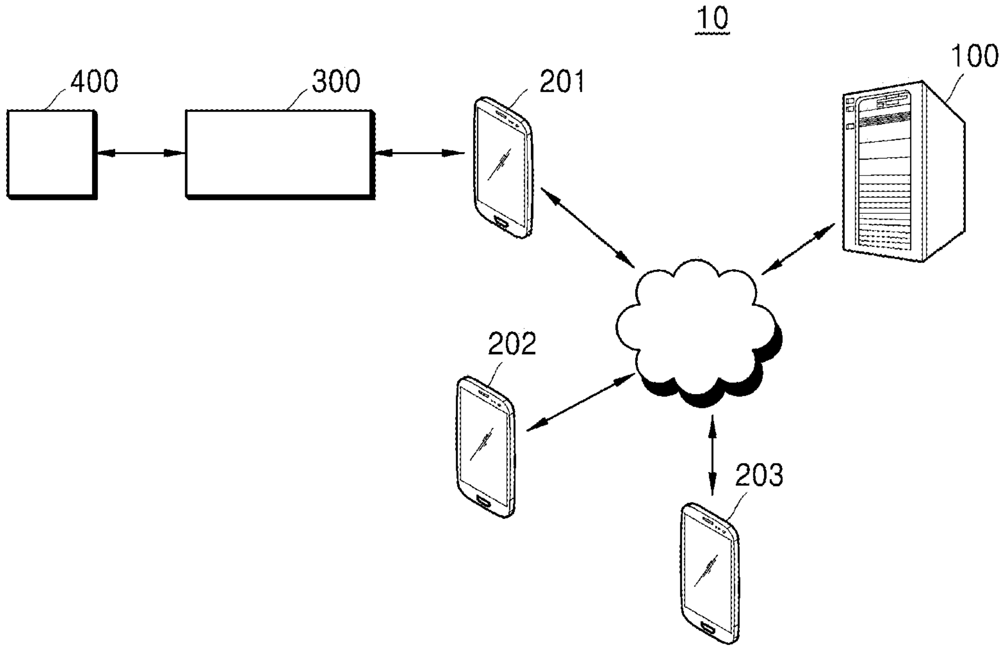
FIG. 1 is a block diagram of a diabetes management system including a management server, a user terminal, a controller, a drug injection device, and a communication network.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

FIG. 1 is a block diagram of a diabetes management system 10 including a management server 100, a user terminal 200, a controller 300, a drug injection device 400, and a communication network 500.

The management server 100 is connected to the user terminal 200 through a communication network and may transmit/receive data. The management server 100 receives data from the user terminal 200 and also generates risk information by combining data. The risk information generated by the management server 100 may include a risk that has already occurred and a risk that will occur in the future. In particular, the management server 100 may provide information about a risk that may occur in the future to other users than a first user, by applying risk symptom information inferred and reasoned from information on a risk happened to the first user who is connected through a communication network, as well as risk information for individual users. The management server 100 not only provides customized risk data applied to individual users, but also provides comprehensive risk data for all managed users.

The user terminal 200 refers to a communication terminal capable of using a web service in a wired/wireless communication environment. Here, the user terminal 200 may be a user's personal computer or a user's portable terminal. Although FIG. 1 shows the portable terminal as a smartphone, but the present disclosure is not limited thereto, and as described above, a terminal equipped with an application capable of performing Internet communication may be adopted without limitation.

In more detail, the user terminal 200 may include, but is not limited to, a computer (e.g., a desktop computer, a laptop computer, a tablet, etc.), a media computing platform (e.g., a cable, a satellite set-top box, a digital video recorder), a handheld computing device (e.g., a PDA, an email client, etc.), any type of a mobile phone, or any other type of computing or communication platform.

The user terminal 200 may be connected to a controller 300 registered in advance in one-to-one correspondence. Also, the user terminals 200 may receive data from the controller 300 in order to prevent control from an external device. The user terminal 200 may transmit setting information, for example, system time information, to the controller 300 within a preset range.

The controller 300 performs data transmission/reception with the drug injection device 400, that is, may transmit a control signal regarding injection of a drug such as insulin to the drug injection device 400 and may receive a control signal regarding a measurement of a biometric value such as blood sugar from the drug injection device 400. The controller 300 may determine whether risk alarm setting information is generated from the user terminal 200. The controller 300 may determine whether the risk alarm setting information is generated by using data such as a drug injection message, a biometric value measurement message, and a device state message from the drug injection device 400.

The controller 300 may transmit an instruction request to measure the current state of the user to the drug injection device 400, and receive measurement data from the measurement device 400 in response to the instruction request.

Here, the drug injection device 400 performs a function of measuring the biometric value such as user's blood sugar value, blood pressure, heart rate, etc., but also performs a function of injecting medicine such as insulin, glucagon, anesthetic, pain killer, dopamine, growth hormone, non-smoking aids, etc. to be injected to the user.

The drug injection device 400 may further include a configuration for storing a substance that is to be periodically injected to the user, and the injection amount that is to be injected may be controlled according to an injection signal generated by the controller 300.

Here, the drug injection device 400 may transmit information such as a measured value and an injection amount to the controller. Selectively, the drug injection device 400 may transfer a device state message, a biometric value measurement message, a drug injection message, etc. to the controller. For example, the drug injection device 400 may transmit a device state message including information about a remaining battery capacity of the device, whether the device is booted successfully, whether the injection is successful, etc. to the controller. Messages transmitted to the controller 300 may be transmitted to the user terminal 200 via the controller 300. Alternatively, the controller 300 may transmit improved data obtained by processing the received messages to the user terminal 200.

The drug injection device 400 may also be implemented to communicate only with a pre-registered controller. In addition, the drug injection device 400 may include an injection device related to the injection. As shown in FIG. 1, although the injection device is included in the drug injection device 400, the injection device performing the injection function may exist separately from the drug injection device 400. The controller 300 may be respectively connected to the injection device and the measurement device to generate and provide a control signal with respect to the injection device based on a measurement value measured by the measurement device.

Figure 2:
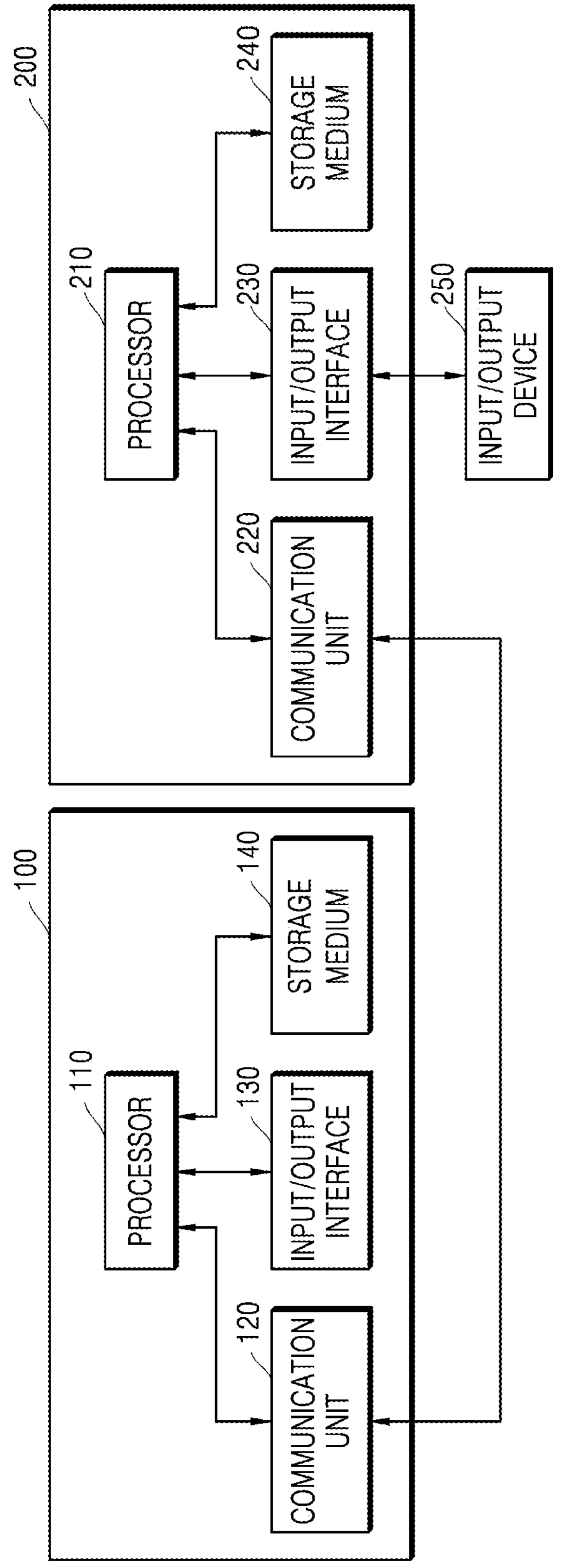
FIG. 2 is a block diagram for illustrating an internal configuration of a management server and a user terminal.

FIG. 2 is a block diagram of the internal configuration of the management server 100 and the user terminal 200. In FIG. 2, the internal configuration of one user terminal 200 and the management server 100 will be described.

The user terminal 200 and the management server 100 may each include a processor, a communication unit, an input/output device, and a storage medium.

Processors 110 and 210 may be configured to process commands from a computer program by performing basic arithmetic, logic, and input/output operations. The commands may be provided to the processors 110 and 210 by storage media 140 or 240 or communication modules 120 and 220. For example, the processors 110 and 210 may be configured to execute received commands in response to a program code stored in a recording device, such as the storage media 140 and 240.

The storage media 140 and 240 are each a computer-readable recording medium, and may include random access memory (RAM), read only memory (ROM), and a permanent mass storage device such as a disk drive. Also, the storage media 140 and 240 may store an operating system and at least one program code. The above software elements may be loaded from a computer-readable recording medium separate from the storage media 140 and 240, by using a drive mechanism. Such above separate computer-readable recording medium may include a floppy drive, a disc, tape, a DVD/CD-ROM drive, a memory card, etc. In another embodiment, software elements may be loaded to the storage media 140 and 240 through the communication units 120 and 220 instead of the computer-readable recording medium. For example, at least one program may be loaded to the storage media 140 and 240 based on a program (e.g., application as described above) installed by files provided over a network from developers or a file distribution system which provides an installation file of the application.

The communication modules 120 and 220 may provide a function for the user terminal 200 and the server 100 to communicate with each other through a network, and may provide a function for communicating with other user terminals. For example, a request (e.g., a request for a messaging service) generated by the processor 210 of the user terminal 200 according to a program code stored on the recording device such as the storage medium 240 may be transferred to the server 100 via the network according to the control of the communication module 220. On the other hand, a control signal, a command, content, a file, etc. provided according to the control of the processor 110 of the server 100 may be transmitted to the user terminal 200 via the communication unit 120 and the network, and the communication unit 220 of the user terminal 200. For example, a control signal, a command, etc. of the server 100 received through the communication unit 220 may be transmitted to the processor 210 or the storage medium 240, and content, a file, etc. may be transmitted to the storage medium that may be further included in the user terminal 200.

Input/output interfaces 130 and 230 may be units for interfacing with the input/output device 250. For example, an input device may include a device such as a keyboard, a mouse, etc., and an output device may include a device such as a display for displaying a communicating session with an application. In another example, the input/output interfaces 130 and 230 may each be a unit for interfacing with a device, in which input and output functions are integrated, such as a touch screen. In more detail, when the processor 210 of the user terminal 200 processes the command of the computer program loaded on the storage medium 240, a service screen or content configured using the data provided by the server 100 may be displayed on a display via the input/output interface 130 and 230.

Also, in another embodiments, the user terminal 200 and the server 100 may include more elements than those of FIG. 2. However, there is no need to clearly indicate the elements according to the related art. For example, the user terminal 200 is implemented to include at least a part of the above-described input/output device 250 or may further include other elements such as a transceiver, a global positioning system (GPS) module, a camera, various sensors, a database, etc. In more detail, when the user terminal 200 is a smartphone, various elements such as an acceleration sensor or a gyro sensor, a camera, various physical buttons, a button via a touch panel, an input/output port, a vibrator for vibration, etc. included generally in a smartphone may be implemented to be further included in the user terminal 200.

Figure 3:
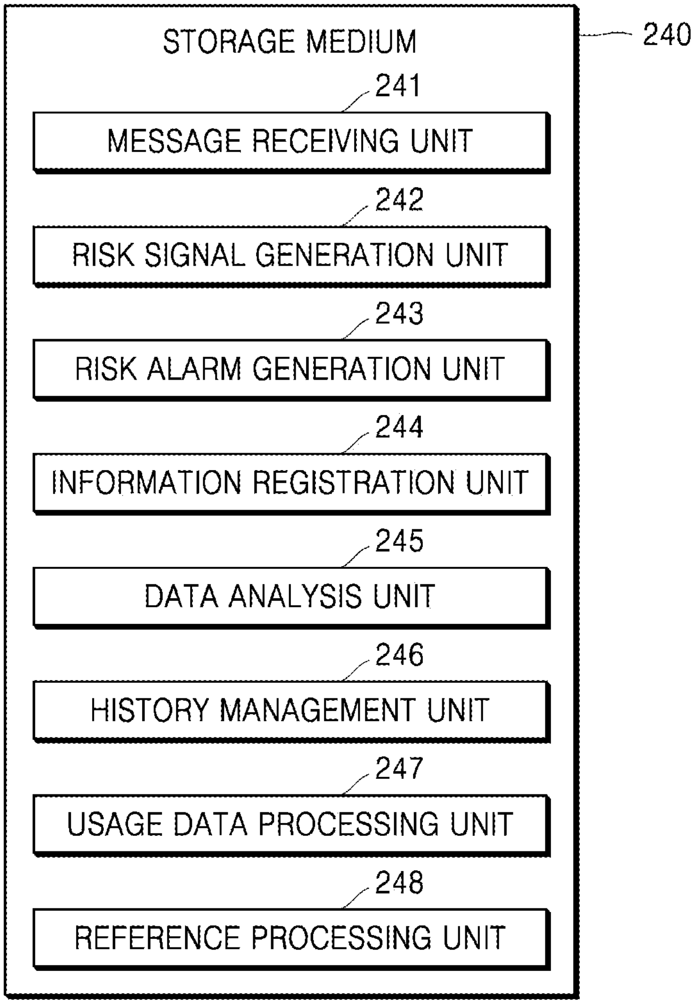
FIG. 3 is a block diagram of a structure in a storage medium of a user terminal according to embodiments of the present disclosure.

FIG. 3 is a block diagram of a structure in the storage medium 240 of the user terminal 200 according to embodiments of the present disclosure.

As shown in FIG. 3, the storage medium 240 of the user terminal 200 may include a message receiving unit 241, a risk signal generation unit 242, a risk alarm generation unit 243, an information registration unit 244, a data analysis unit 245, and a history management unit 246.

The message receiving unit 241 receives a drug injection message, a biometric value measurement message, and a device state message from the controller. The drug injection message refers to information on a drug (insulin) injected to the user through the drug injection device connected to the controller. The drug injection message may include the amount of the injected drug, the amount of the drug remaining after the drug injection, information on ingredients of the drug, product information of the drug, etc.

The biometric value measurement message refers to information about the biometric value (blood sugar value) measured through the drug injection device connected to the controller. The biometric value measurement message may include a measured blood sugar value, a measurement time point, event information before blood sugar measurement, etc.

The device state message refers to a message related to the status of the controller 300 and the drug injection device 400. The device state message is a message including status information of the elements included in the controller 300 and the drug injection device 400, and may include information on the remaining battery capacity, power status information, functional error or error information, additional supplemental information for insulin, e.g., whether the elements operate, whether the elements may possibly operate, etc. For example, information on the remaining battery of the drug injection device 400, information on remaining operable time based on the remaining battery, capacity information of stored drug, information on injectable period of the stored drug, etc. may be generated as the device state message and may be transmitted to the controller 300. In another embodiment, the controller 300 may generate information about remaining operating time based on the remaining battery capacity from the received remaining battery information, or may generate information about injectable period from the received capacity information of the drug.

The risk signal generation unit 242 generates a risk signal by using the drug injection message, the biometric value measurement message, and the device state message received from the controller 300. The risk signal generation unit 242 determines whether a risky situation corresponding to risk alarm setting information occurs, by using the drug injection message, the biometric value measurement message, and the device state message.

The risk signal generation unit 242 may generate a risk signal indicating insufficient injection amount, when the injection amount included in the drug injection message is different from the injection amount registered in advance.

The risk signal generation unit 242 generates a risk signal indicating a blood sugar level being in a danger, when the blood sugar value included in the biological measurement message exceeds a normal blood sugar range.

The risk signal generation unit 242 calculates a remaining usage term based on the remaining battery from among the status values included in the device state message, and when the remaining usage term is less than a minimum usage term set in advance, the risk signal generation unit 242 generates a risk signal indicating the battery replacement.

The risk signal generation unit 242 generates a risk signal regarding booting of the controller by using a booting error included in the device state message.

The risk signal generation unit 242 determines a suitability of the blood sugar value according to the insulin injection amount, in consideration of the blood sugar value included in the biometric value measurement message and the injection amount included in the drug injection message. With respect to the suitability of the blood sugar value, it may be determined whether there is a change in the blood sugar based on the injection amount and a reaction coefficient by comparing a first measurement value that is measured before the injection with a second measurement value measured after the injection. When it is determined that a change occurs in the blood sugar based on the injection amount and the reaction coefficient, a risk signal for additional injection is generated. The risk signal generation unit 242 may further include risk codes according to kinds of the risk signals.

The risk signal generation unit 242 may receive a risk signal corresponding to the risk alarm setting information from the controller 300.

Here, the risk alarm setting information is received by the user or the management server 100.

The risk alarm generation unit 243 generates an alarm, taking into account the risk signals and the risk codes corresponding to the risk signals. The risk signal may be received from the controller or may be generated based on the message received from the controller. The risk alarm generation unit 243 may determine a level of the alarm in consideration of the risk code, select a terminal to receive the alarm based on the level, and transmit the alarm to the selected terminal. The receiving terminal may output an operation according to the corresponding alarm.

In an alternative embodiment, when it is true whether the risky situation occurs, the risk alarm generation unit 243 may transmit the risk alarm message to a terminal of a recipient group that is registered as managers of the user or a risk management center.

When the risk signal is received or generated, the risk alarm generation unit 243 generates a chat room including the recipient group registered as the manager of the user, and controls one-to-one message transmission among participants in the chat room to be impossible, but shares the risk alarm message of the user through the chat room. The risk alarm message may further include location information. The risk alarm message may include a representative name of the processed location. For example, when location information is adjacent to 'home', that is, a previously registered location, the location information is converted into the representative name, that is, home, and may be included in the risk alarm message. Location information located within a certain distance range from location information registered as 'work' is converted into 'work' and may be included in the risk alarm message. As such, it is possible to remove a situation in which it is difficult to determine an accurate location due to an error in location information. The risk alarm message may include both location information and a representative name of the location information.

In addition, the risk alarm message may be implemented so that an additional alarm is generated at a preset time point. Here, a time point of generating the additional alarm varies according to golden time of the risk signal.

The risk alarm generation unit 243 may convert a standby screen of the user terminal into an emergency card screen and provide the screen. When the user is in a critical condition, along with the transmission of the risk alarm message, the standby screen of the user terminal is converted into the emergency card screen such that emergency treatment may be performed by people around the user. The emergency card screen includes information set by the user, and may be implemented to include, for example, the user's disease, necessary measures, etc. In addition, the emergency card screen may be implemented to include a phone number of the user's guardian. The emergency card screen may be provided according to the recognized biometric information. For example, when the user's biometric information is recognized while the user terminal is locked, a general standby screen is output instead of the emergency card screen, and when the biometric information of another user is recognized, the emergency card screen may be provided while maintaining the locked state.

The information registration unit 244 allows the user to register personal information. The registered personal information may include other items such as user name, gender, age, height, weight, occupation, race, blood type, diabetes type, etc. The setting information registered through the information registration unit 244 is synchronized with the management server 100. The setting information may be used in an offline state during which synchronization with the management server 100 is not performed. The information registration unit 244 may receive the risk alarm setting information.

The data analysis unit 245 generates analysis data for the user's disease, such as diabetes, based on the messages received through the controller. The data analysis unit 245 generates statistical data related to the drug (insulin) injection by using the drug injection message. The data analysis unit 245 generates statistical data related to the measurement of the biometric value (blood sugar) by using the blood sugar value measurement message. An analysis option for generating analysis data may be registered in advance. The analysis option may include a blood sugar unit, time system setting information, time zone setting information, etc. The time system setting information may be a 12-hour system or a 24-hour system. The time zone setting information may store morning, afternoon, evening, and sleep time information according to the user's actual lifestyle. For example, the sleep time information may be set as first sleep time, e.g., from 10 pm to 6 am, or second sleep time, e.g., from 12 pm to 8 am. In correspondence with the first sleep time, the morning time may be set to be from 6 am to 11 am. In correspondence with the second sleep time, the morning time may be set to be from 8 am to 1 pm. The time point of measuring the blood sugar and the time point of injecting insulin may individually vary depending on the time zone setting information of the user.

The history management unit 246 may generate history of user's health management based on the drug injection message and the biometric value measurement message from the controller connected thereto. The health management history may manage measured blood sugar values by listing them in the time serial order, and may monitor whether the blood sugar values are greater than a target blood sugar value and whether the blood sugar values exceed the target blood sugar range.

The history management unit 246 may manage a history of alarms generated in relation to a risky situation.

The storage medium 240 of the user terminal 200 may further include a usage data processing unit 247.

The usage data processing unit 247 may restrict execution of a drug injection program according to the management server or a preset condition. For example, when it is detected that a pre-paid usage amount is exceeded, the usage data processing unit 247 may generate an event in which the use of the drug injection program is restricted and change the state of the drug injection program to an inactive state. The usage data processing unit 247 may perform an additional payment process according to the usage data. The usage data processing unit 247 transmits usage data to the management server in the drug non-injection time according to a request from the management server, and receives a payment link of the usage fee corresponding to the usage data from the management server. When payment and approval of the usage fee corresponding to the user data through the payment link are finished, the drug injection program, which has been restricted in use, may be executed immediately.

A reference processing unit 248 may acquire information related to an insulin injection amount that may be used in a specific situation through the management server. The reference processing unit 248 may transmit data of insulin injection or blood sugar measurement to the controller 300 based on the acquired data. When the blood sugar value corresponds to the risk of hypoglycemia or the risk of hyperglycemia, the reference processing unit 248 requests, to the management server, information on the insulin injection amount for removing the hypoglycemia risk or hyperglycemia risk, receives a payment link for disclosure of information received from the management server, and when the payment through the payment link is approved, the reference processing unit 248 receives the insulin injection amount information for removing the risk, and may transmit the insulin injection amount information for removing the risk to the controller that is connected thereto in advance. When there is a newly released insulin product, the reference processing unit 248 may obtain a reaction coefficient for each product, etc. from the management server. The reference processing unit 248 has to perform appropriate payment accordingly.

The user terminal 200 may receive data from the controller using the drug injection program, and may use an updated algorithm after installation, after payment of a predetermined amount. In addition, the user terminal 200 may perform payment according to the usage period, usage amount, etc. of the drug injection program. The drug injection program may be downloaded free of charge upon installation, and payment can be made by continued use. When data on disease management and drug injection are accumulated through the user terminal 200, the above data may be used in connection with various services such as reduction of insurance premiums, reduction of medical expenses, and reservation of medical treatment, etc.

The user may access the management server through another user terminal, and may be provided with the same screen provided to the user terminal. Here, a user authentication process using user identification information is performed.

Figure 4:
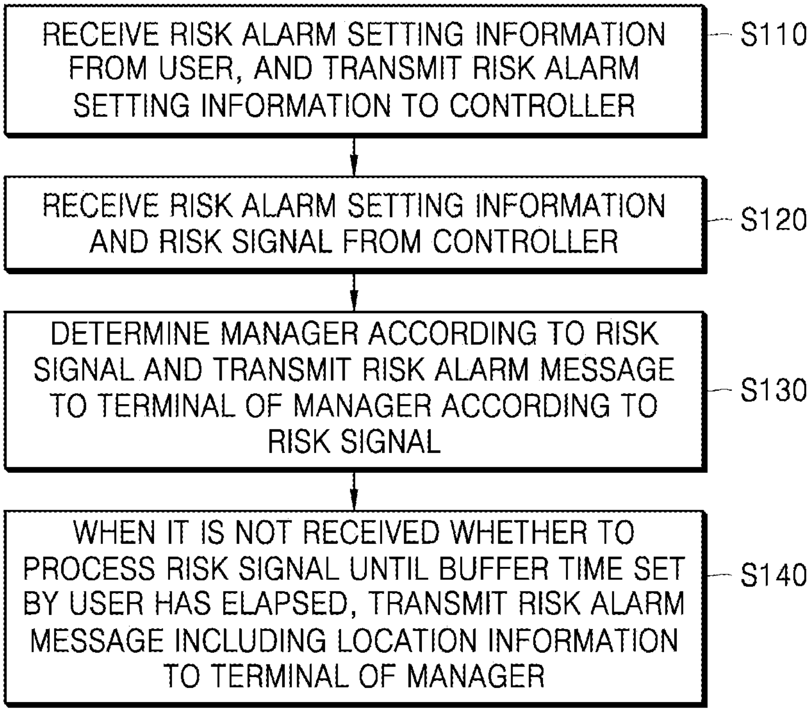
FIGS. 4 to 6 are flowcharts for describing a method of managing a state after automatically injecting a drug, in a user terminal on which a diabetes management application is installed and which communicates with a controller that is connected to a drug injection device related to insulin injection.
Figure 5:
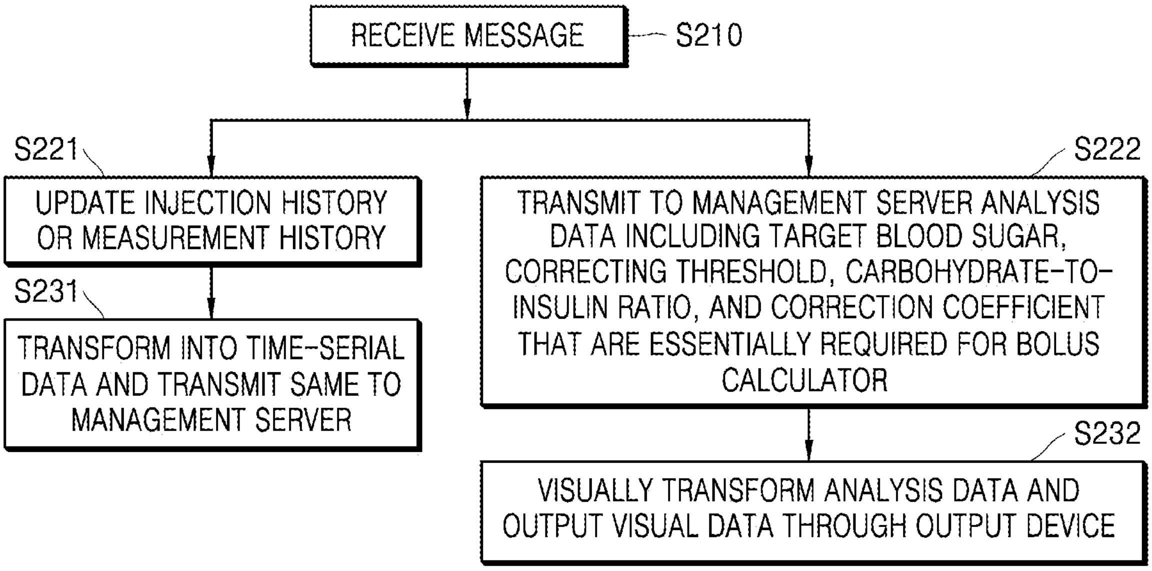
Figure 6:
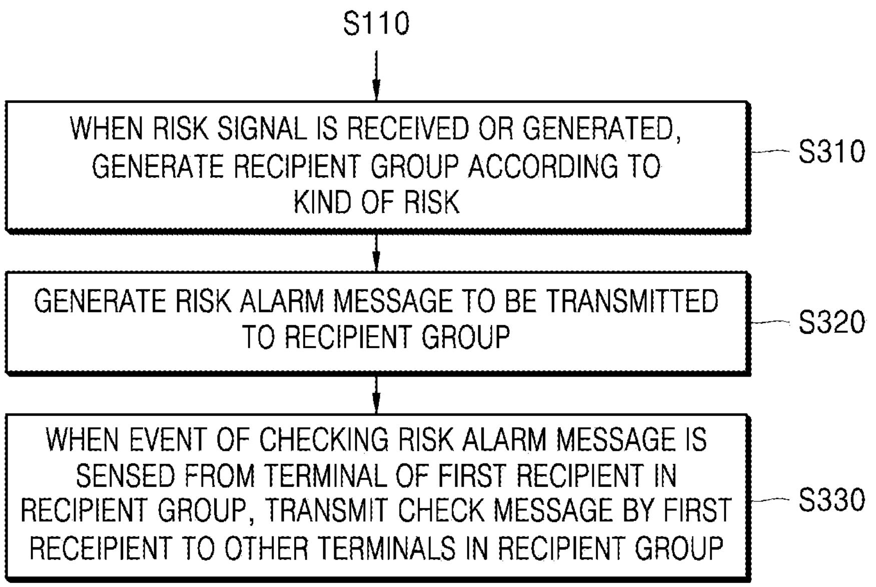

FIGS. 4 to 6 are flowcharts illustrating a method of operating the user terminal 200, on which a diabetes management application is installed and which communicates with a controller that is connected to a drug injection device related to the insulin injection. The user terminal 200 executes a computer program installed thereon from the management server 100 and performs a function of analyzing a real-time drug injection message from the controller.

As shown in FIG. 4, in S110, the user terminal 200 for diabetes management receives risk alarm setting information that is information related to an alert and a reminder, from the user. Here, the risk alarm setting information may include at least one from an alert for automatic injection block, an alert for a patch expiration, an alert for insufficient insulin, a reminder for basic blood sugar checking, a reminder for a meal bolus, and a reminder for user setting. The alert for automatic injection block may occur when the user does not use the controller within a preset time period and patch information is not obtained. The alert for patch expiration may occur when the remaining use period of the patch is equal to or less than a period set by the user. The alert for insufficient insulin may occur when an insulin stock amount is equal to or less than a dose set by the user. The reminder for basic blood sugar checking occurs when the blood sugar value is not measured at every measurement cycle set by the user. The reminder for meal bolus occurs when a bolus injection is not performed within a time range set by the user.

Additionally, in S110, the user terminal 200 may transmit the risk alarm setting information from the user to the controller.

In S120, the user terminal 200 may receive a risk signal corresponding to the risk alarm setting information from the controller. The risk signals (alarm and alert) may be generated by the controller.

In S130, the user terminal 200 may determine a manager according to the risk signal, and transmit a risk alarm message to a terminal or a management server of a recipient group registered as a manager according to the risk signal. When the user terminal 200 does not receive, after the received risk signal, an instruction whether to process the risk signal until a certain time (buffer time) set by the user has elapsed, the user terminal 200 may transmit the risk alarm message including location information to the terminal of the manager or the risk management center. The manager's terminal is preset by the user, and is set as a terminal of a user having management authority over the user, e.g., a spouse, parents, medical staffs, etc. of the user.

FIG. 5 is a flowchart of a method of managing a state after automatically injecting a drug according to embodiments of the present disclosure.

As shown in FIG. 5, in S210, the user terminal 200 receives a drug injection message, a biometric value measurement message, and a device state message from the controller.

In S221, the user terminal 200 updates injection history or measurement history. In S231, the user terminal 200 converts the injection history or the measurement history into time-serial data and transmits the time-serial data to the management server 100. In S222, the user terminal 200 transmits to the management server the analysis data including a target blood sugar, a correction threshold, a carbohydrate-to-insulin ratio, and a correction coefficient that are essential for a bolus calculator. In S232, the user terminal 200 receives the data analyzed by the management server 100 from the management server 100, converts the analyzed data into data that is visually output, and outputs the data through an output device.

The user terminal 200 provides the user's data received from the controller to the management server 100 for generating analysis data for diabetes management. The users data may include terminal personal information (age, gender, height, weight, etc.), a blood sugar value, an insulin injection amount, etc.

As shown in FIG. 6, in S310, when a risk signal is received or generated after operation S110, the user terminal 200 creates a recipient group according to the type of risk.

In S320, the user terminal 200 may generate a risk alarm message to be transmitted to the recipient group. In another embodiment, the user terminal 200 may transmit the received or generated risk signal to the management server 100, and may receive a risk alarm message from the management server 100 and transmit the risk alarm message to the recipient group. The risk alarm message may include information on a user who is in danger, and information on a risky situation that occurs. The information about the user may include identification information of the user such as the user's name, nickname, and identification (ID), and automatically sensed location information or location information input by the user. The information on the risky situation may include the type of risk that has occurred, the time of occurrence of the risk, recommendations for each risk, golden time, etc.

In S330, when an event in which a terminal of a first recipient in the recipient group identifies the risk alarm message is sensed, the user terminal 200 may transmit a confirmation message by the first recipient to the remaining terminals of the recipient group. The confirmation message may be generated based on information input by the first recipient, or may be automatically generated by a user input through the terminal of the first recipient.

The confirmation message may include information about arrival time until the first recipient reaches the user in danger.

When a second recipient is found from the recipient group, the second recipient being capable of reaching the user faster than the above arrival time information, the user terminal 200 transmits a query message, that is, 'Do you want to reach the user faster than the first recipient?' to a terminal of the second recipient, in order to guide the second recipient to process the risky situation of the user, in which health management such as diabetes management or a drug injection management is required.

A recipient group may be managed through one group chat room, and when a risky situation occurs, a chat room for sharing a message with the recipient group may be created. Each terminal of the recipient group may communicate with the others through the created chat room. Here, the first recipient and the second recipient who know each other in the recipient group may directly send/receive messages one-to-one with each other, but the first recipient and a third recipient who do not know each other may only receive the messages and may not send/receive messages one-to-one with each other.

In another embodiment, the user terminal 200 may sequentially transmit the risk alarm message in the order of the distances from the user. For example, the user terminal 200 transmits the risk alarm message with the top priority to the terminal of the first recipient located at the closest distance, and transmits the risk alarm message with the last priority to the terminal of the second recipient located at the farthest distance.

FIGS. 7 to 15 are diagrams showing examples of a user interface provided by the embodiments of the present disclosure.

Figure 7:
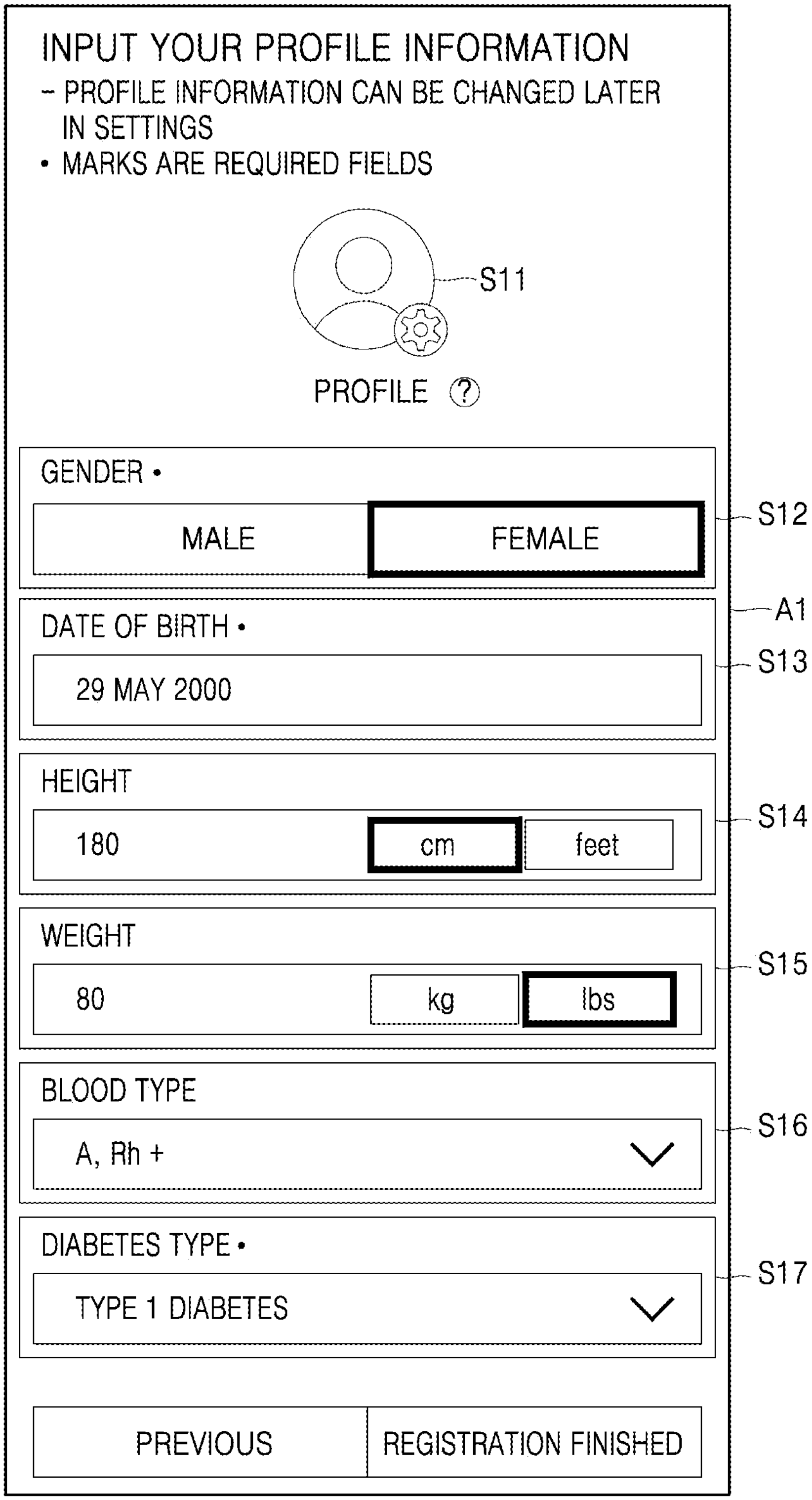
FIGS. 7 to 15 are diagrams showing examples of a user interface provided according to embodiments of the present disclosure.

As shown in FIG. 7, a setting information input screen A1 includes a profile picture input region S11, a gender input region S12, a date of birth region S13, a height input region S14, a weight input region S15, a blood type input region S16, and a diabetes type input region S17. The diabetes type input area S17 includes either type 1 diabetes or type 2 diabetes. The management server 100 or the user terminal 200 may determine a relational expression for calculating the insulin injection amount using the setting information.

Figure 8:
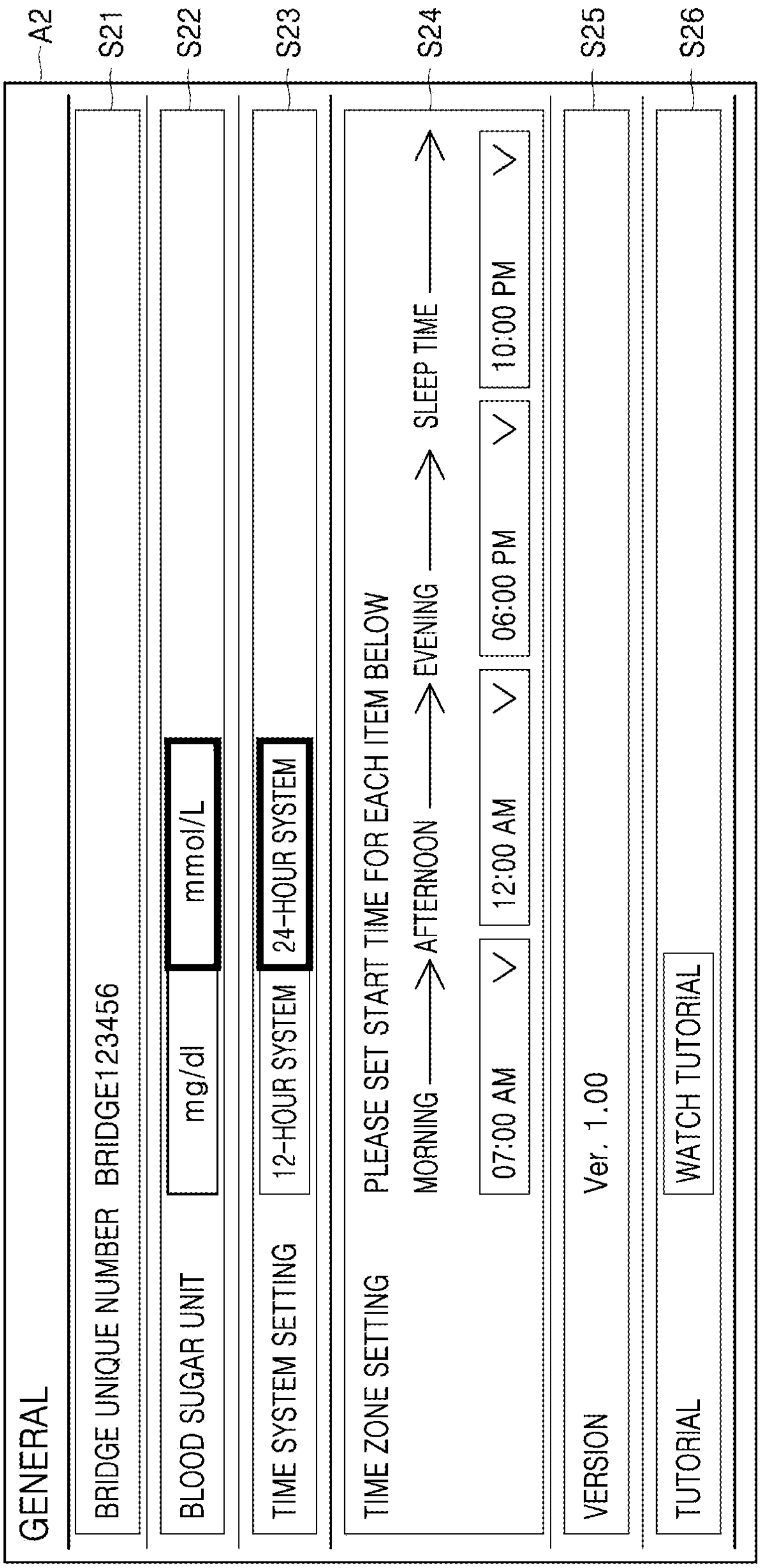

As shown in FIG. 8, an analysis option screen A2 includes a bridge unique number region S21, a blood sugar unit region S22, a time system setting information region S23, a time zone setting information region S24, a version information region S25, and a watch-tutorial region S26. The bridge unique number region S21 may provide identification information of the connected controller. The blood sugar unit region S22 provides information about used units of the blood sugar level. The time system setting information region S23 may include either a 12-hour system or a 24-hour system. The time zone setting information region S24 may set morning time, afternoon time, evening time, and sleep time according to life pattern of each user.

Figure 9:
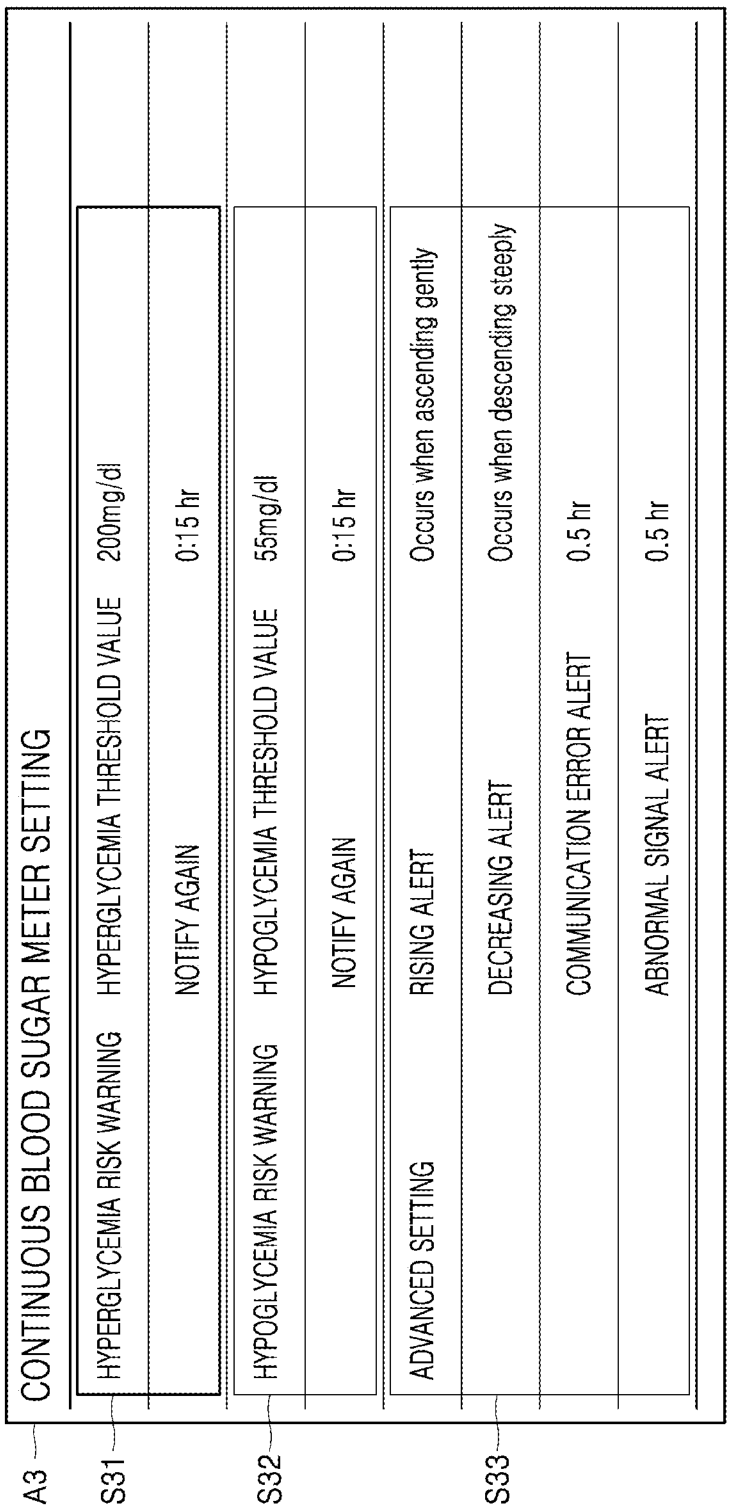

As shown in FIG. 9, a continuous blood sugar meter setting screen A3 may include a hyperglycemia risk warning region S31, a hypoglycemic risk warning region S32, and an advanced setting region S33.

The hyperglycemia risk warning region S31 may include a hyperglycemia threshold value and an alarm message generation time when blood sugar value above the hyperglycemia threshold is detected. The hyperglycemia threshold value may be obtained by downloading information set and pre-registered by a user having the authority of setting the risk information.

The hypoglycemic risk warning region S32 may include a hypoglycemia threshold value and an alarm message generation time when blood sugar value below the hypoglycemic threshold is detected. The hypoglycemia threshold value may be obtained by downloading information set and pre-registered by a user having the authority of setting the risk information.

The advanced setting region S33 is a region for outputting a condition of occurring rising alert, a condition of occurring a decreasing alert, a condition of occurring a communication error alert, and a condition of monitoring a signal error alert.

The conditions for occurrence of the rising alert, the decreasing alert, the communication error alert, and the signal error alert are set by the user having the authority of setting the risk and may be downloaded from the management server 100.

The user terminal 200 may monitor whether the condition for occurrence of the alert for the blood sugar value is generated based on the messages received from the controller. When the change in the blood sugar value matches the occurrence conditions, the user terminal 200 generates a risk alarm message of the rising alert or the decreasing alert. The user terminal 200 may receive the risk signal from the controller and generate the risk alarm message corresponding to the risk signal. When a failure occurs in communication with the controller, the user terminal 200 generates a risk alarm message indicating the communication error alert. When an abnormality of the received signal occurs, the user terminal 200 generates an alarm message indicating the signal error alert. When the received signal is not interpreted based on a predefined protocol and when the received signal is identified to be generated by an abnormal controller, the risk alarm message indicating the signal error alert is generated.

Figure 10:
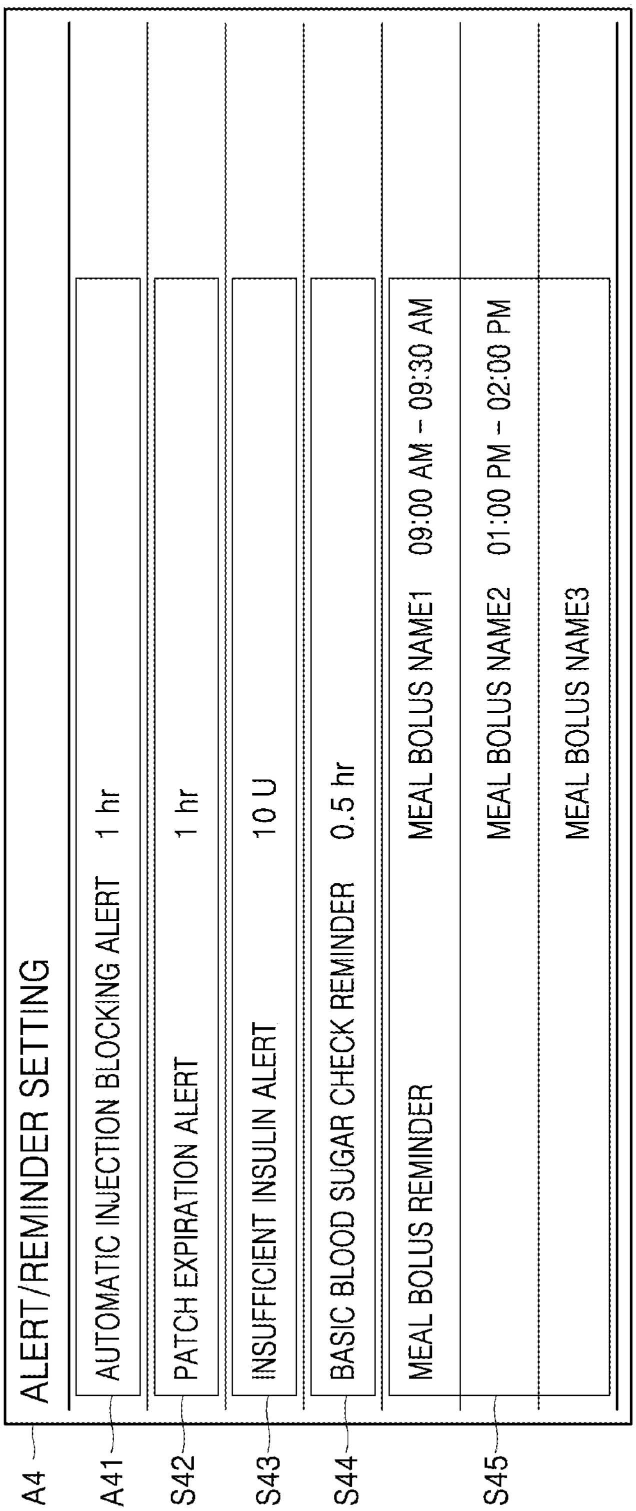

As shown in FIG. 10, an alert/reminder setting screen A4 may include an automatic injection block alert region S41, a patch expiration alert region S42, an insufficient insulin alert region A43, a basic blood sugar checking reminder region S44, and a meal bolus reminder region S45.

Figure 11:
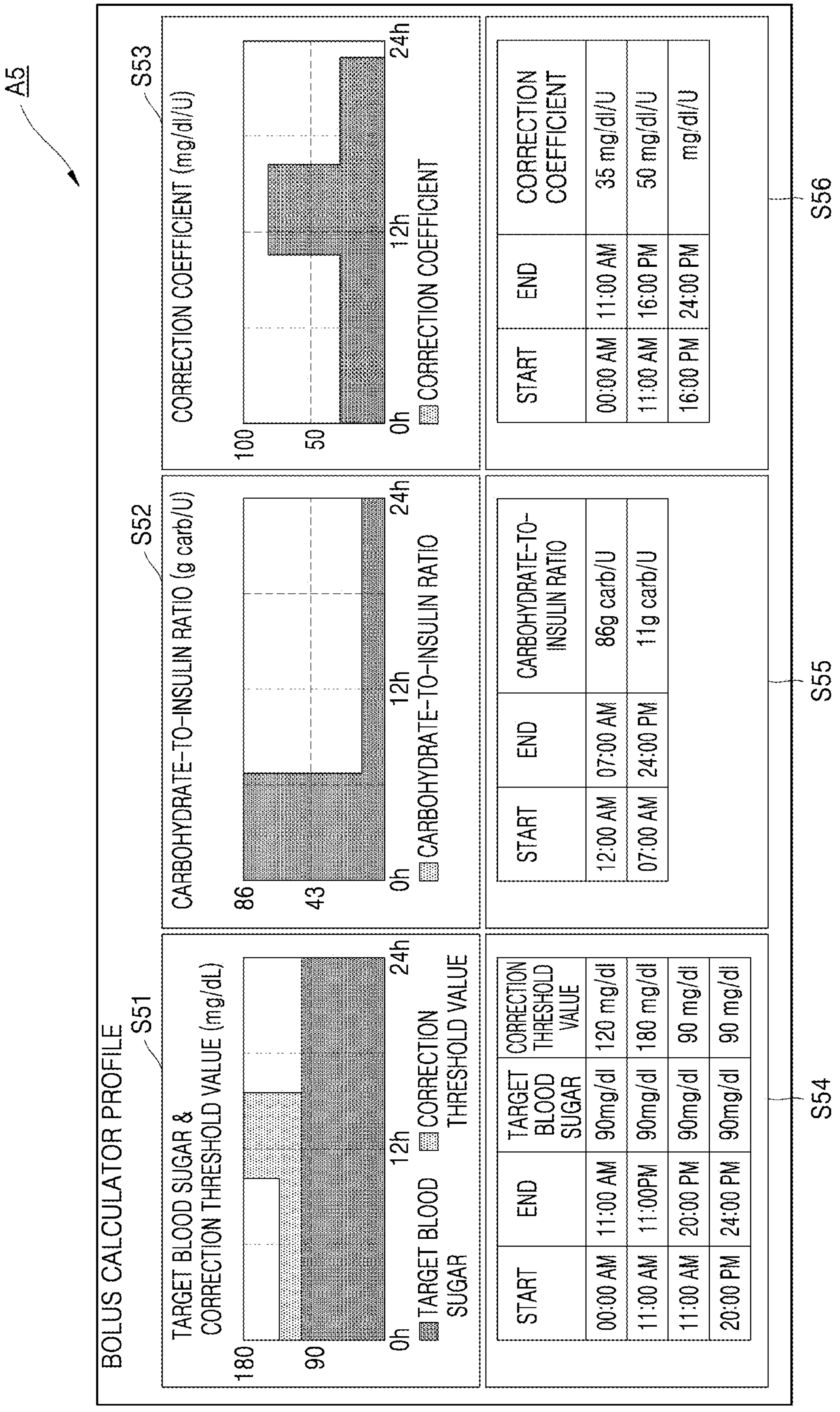

As shown in FIG. 11, a bolus calculator screen A5 may include a region S51 showing a relation between a target blood sugar and a correcting threshold, a carbohydrate-to-insulin ratio S52, and a correcting coefficient region S53.

Figure 12:
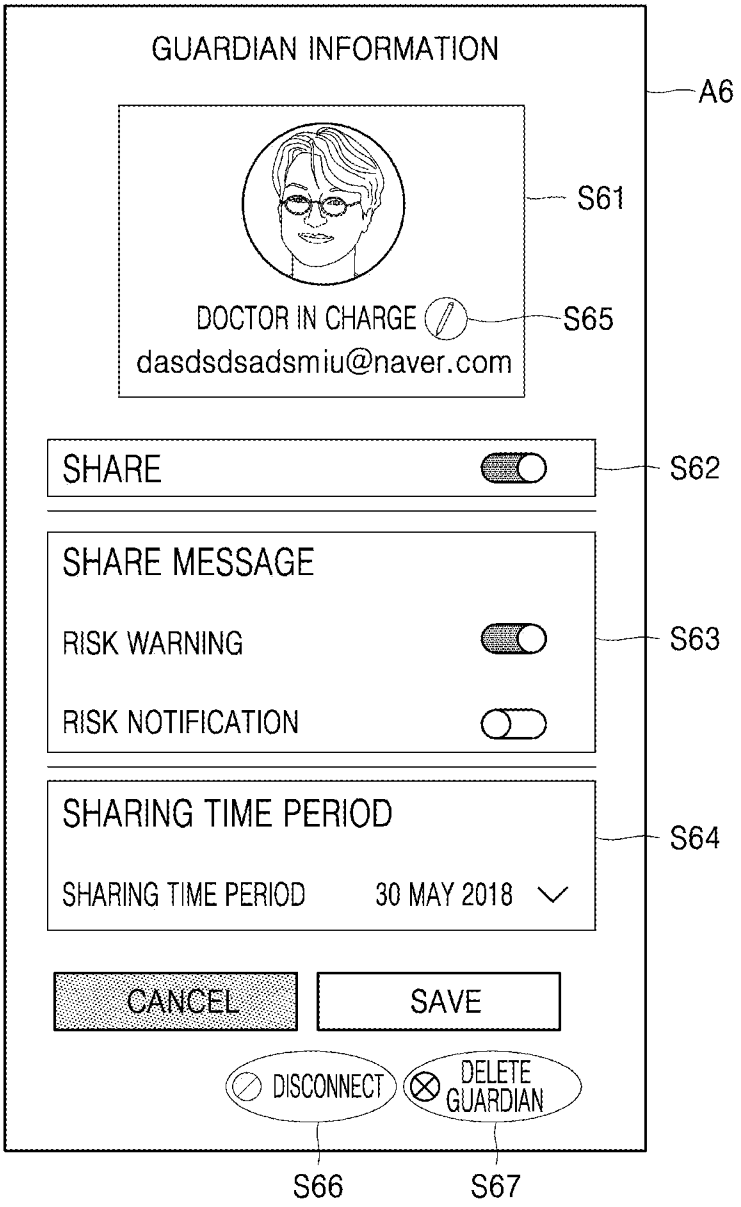

As shown in FIG. 12, a guardian information input screen A6 may include a profile region S61, a share region S62, a message share region S63, and a sharing period region S64.

The profile region S61 is a region for providing profile information of a manager of the user. S65 may be selected to go to an edit section.

The share region S62 provides an icon representing whether there is information to be shared. The manager's authority on the user may be maintained for the sharing period. When the sharing period expires, it may be set not to send an alarm message to the corresponding manager. Manager information, of which sharing period has expired, may be checked through a manager list screen by period even after the sharing period.

The guardian information input screen A6 may include a disconnection icon S66 and a guardian delete icon S67. Through the disconnection icon S66, it is possible to set that the alarm is not temporarily transmitted even within the sharing period. When the guardian delete icon S67 is selected, an event of deleting the guardian occurs and is transmitted to the management server 100.

When an approval confirmation signal is received from the management server 100, the corresponding guardian may be deleted.

Figure 13:
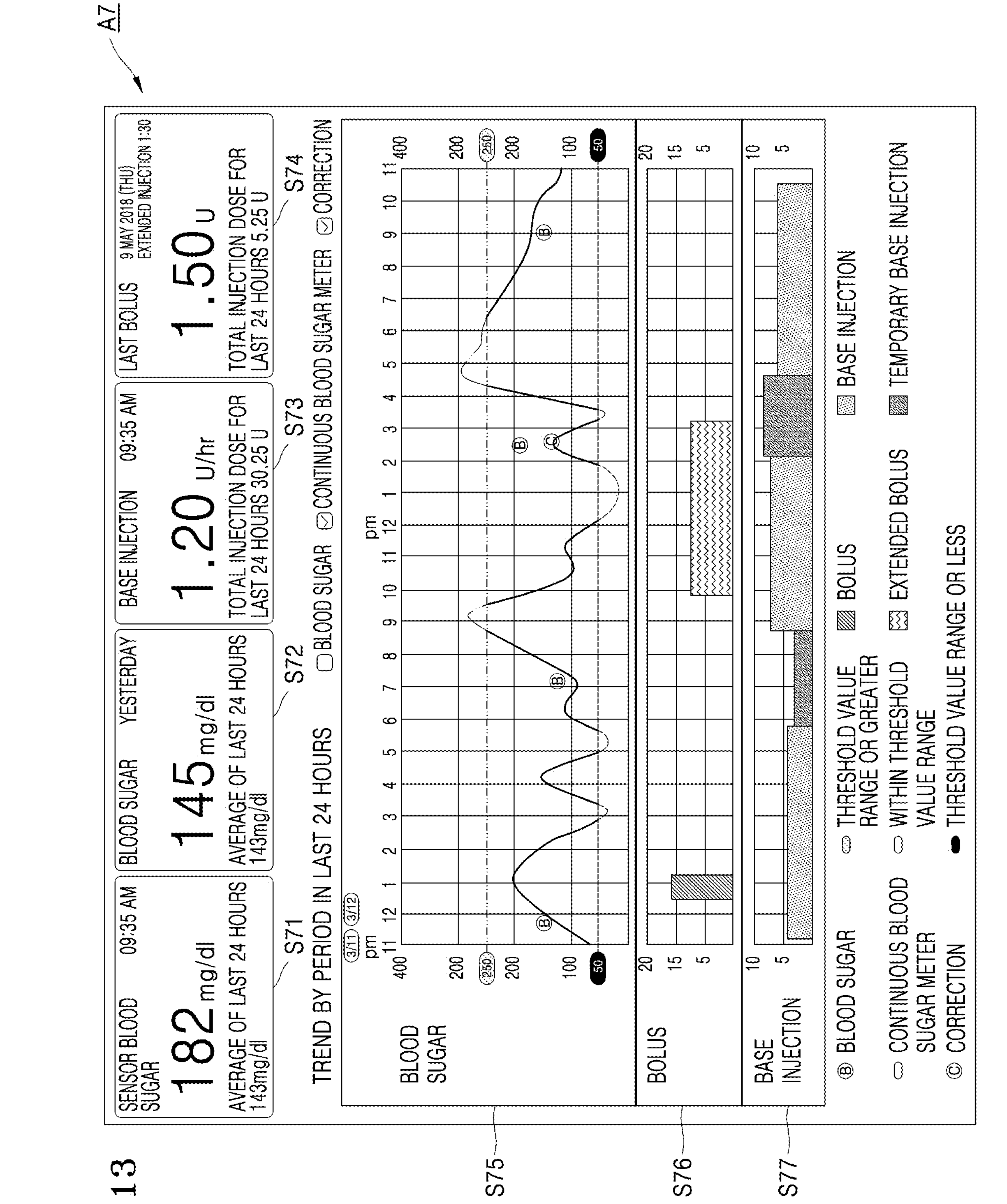
Figure 14:
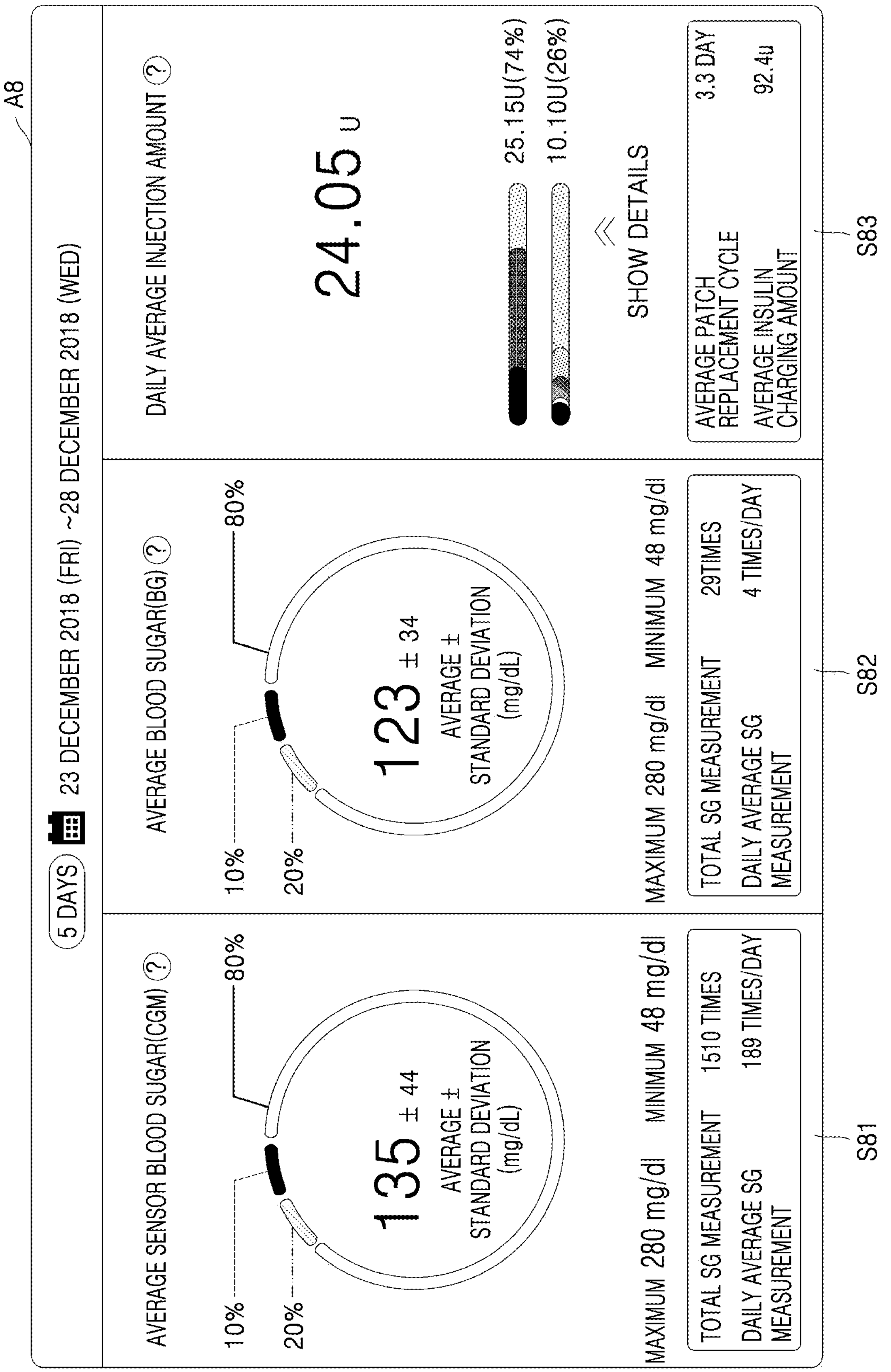

FIGS. 13 and 14 are diagrams showing examples of analysis data provided through the user terminal 200.

As shown in FIG. 13, a first analysis data providing screen A7 may include a region S71 for providing a blood sugar value measured through the connected drug injection device 400, a region S72 for providing an average blood sugar value, a region S73 for providing a base injection amount of insulin, and a region S74 for providing a last injection amount.

The first analysis data providing screen A7 may provide a change in blood sugar S75, an insulin injection amount S76, and a base insulin injection amount S77 in linkage with one another by time.

As shown in FIG. 14, a second analysis data providing screen A8 may numerically provide information on an average sensor blood sugar, an average blood sugar, and a daily average injection amount, etc., and an average sensor blood sugar S81 denotes a blood sugar value measured by a blood sugar sensor and may be indicated in an average and standard deviations along with a daily average number of measuring times.

An average blood sugar S82 refers to a blood sugar value measured through a separate measurement device.

A daily average injection amount S83 may include statistical data such as an average patch replacement cycle, an average insulin filling amount, etc. along with a maximum value and a minimum value.

Figure 15:
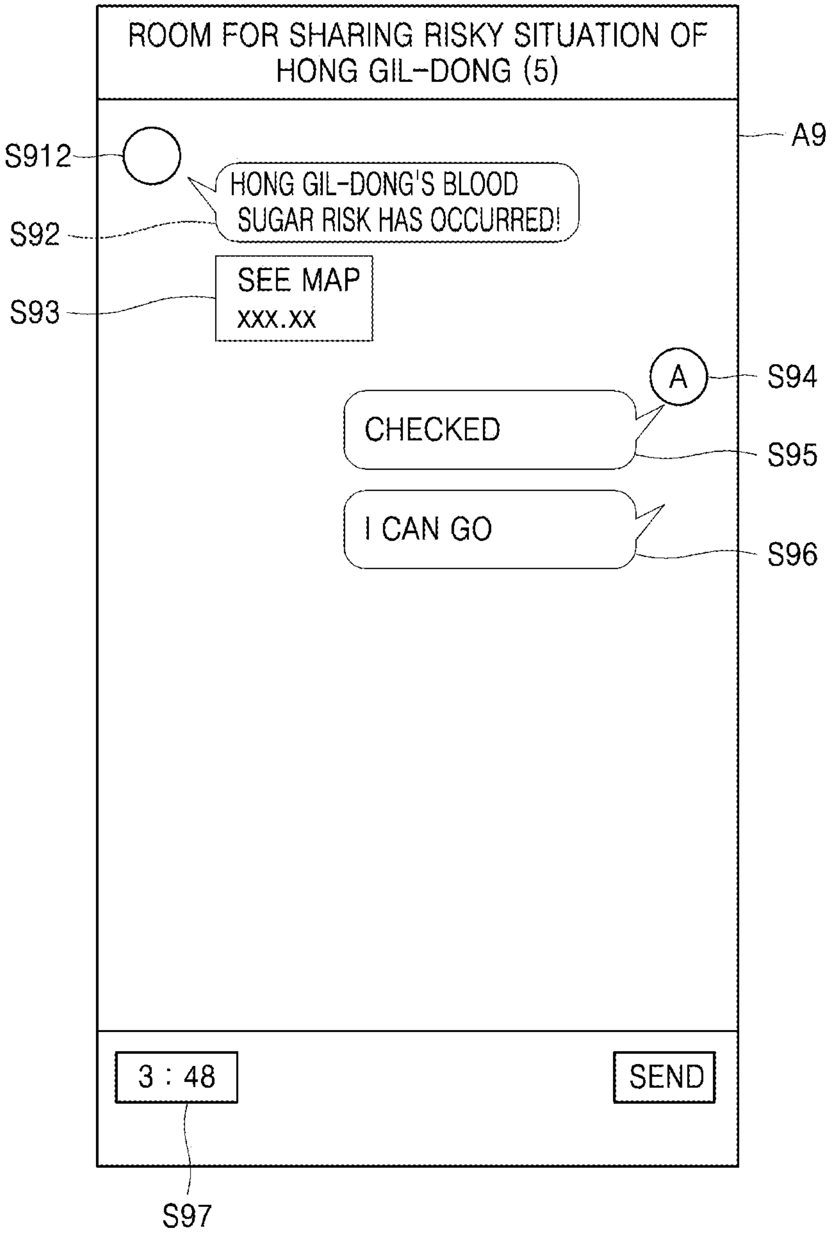

FIG. 15 is a diagram showing an example of a chat room screen in which a risk message is shared by the user terminal 200. The chat room may be automatically created and managed based on the manager information of the user. The chat room may be created when an alarm message to be transmitted to managers is generated or when a risky situation of the user occurs. When the risky situation disappears, the chat room disappears.

A chat room screen A9 provides a message S92 indicating that a risk in a blood sugar level of Hong Gil-dong has occurred and a map view icon S93 showing location information of the user, by a manager icon S912 of the chat room. When a participant in the chat room selects the map view icon S93, a map on which the user's location is spotted may be provided.

Messages S95 and S96 input by a first recipient from among the participants of the chat room may be shared along with an icon S94. The participants may only send messages through the chat room.

A region S97 for displaying information on elapsed time after the occurrence of the risky situation may be further provided. When the time provided in the region S97 coincides with a preset threshold time, it may be controlled to generate an additional alarm (sound, vibration, message, etc.). As such, the managers may share the risky situation of the user, and by providing the information on the elapsed time after the occurrence of the risky situation through the chat room or the main screen, it may be managed not to continue the risky situation of the user.

Figure 16:
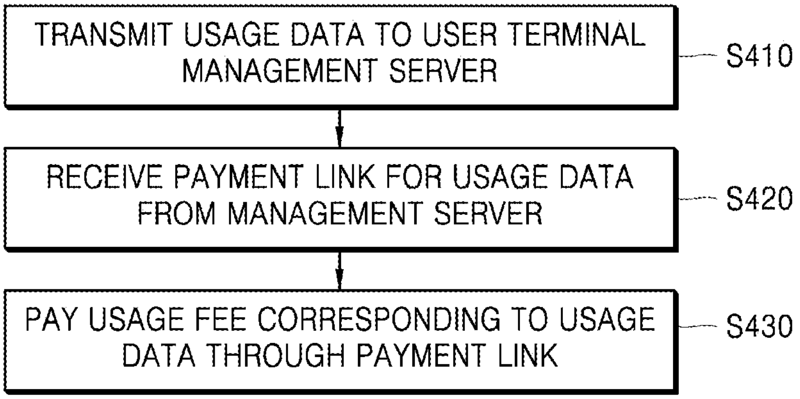
FIG. 16 is a flowchart for describing a method of managing the status after automatically injecting a drug in a user terminal according to another embodiment of the present disclosure.

As shown in FIG. 16, in S410, the user terminal 200 transmits usage data to the management server 100. The usage data may include usage data for the drug injection device 400, usage data of the controller 300, and/or usage data of the user terminal. The transmission time point may be set in the management server 100.

In S420, the user terminal 200 receives a payment link for usage data from the management server 100. In S430, when an operation of paying usage fee corresponding to the usage data through the payment link is performed, the user terminal 200 may execute the drug injection program. When the usage fee is not paid, the drug infusion program is not executed and continues to be suspended.

Figure 17:
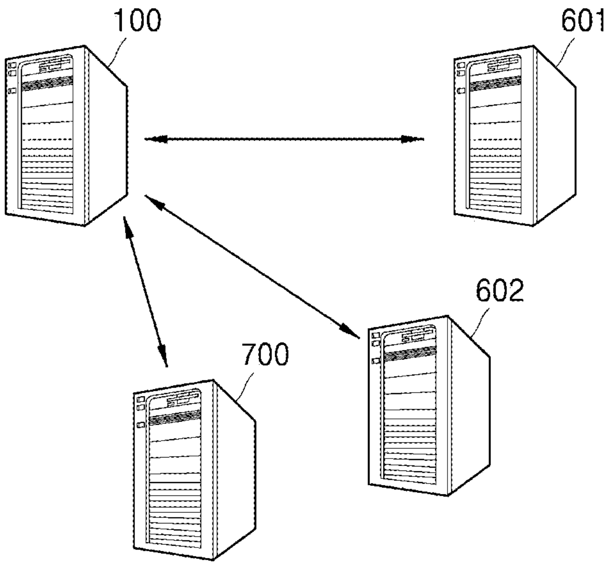
FIG. 17 is a diagram for describing an additional process for processing data transmitted to a management server.

FIG. 17 is a diagram for describing an additional process of processing data transmitted to the management server 100.

The diabetes management system 10 may transmit the usage data and analysis data collected to the management server 100 to an insurance company server 601 or a cloud server 602, that is, another external server.

The insurance company server 601 may recalculate the insurance premium of a diabetic patient based on the usage data and the analysis data collected through the drug injection program of the diabetic patient. For example, the insurance premium of the patient may increase or decrease based on whether the drug injection device is used, the period of use, the change in the blood sugar value, etc.

The cloud server 602 calculates predetermined data usage cost according to a signal requesting the usage data or analysis data of the diabetic patient, and sells the usage data or analysis data after the payment of the data usage cost. The cloud server 602 may transmit to a server of a medical institution, e.g., a hospital, a pharmacy, etc. the diabetes management usage data of each user or analysis data. Through a predetermined authentication procedure for the cloud server 602, it is possible to access the usage data or analysis data of individual users.

The management server 100 may update the diabetes management program through a CNN transformation server 700. The CNN transformation server 700 may individually calculate key factors required for the bolus calculator, e.g., base injection setting information, an insulin correction response coefficient, an insulin duration time, a carbohydrate-to-insulin ratio, etc. based on the usage data and analysis data collected through the diabetes management program. As the usage data and analysis data are accumulated, the diabetes management program is optimized.

Through the above processes, the CNN transformation server 700 calculates a reaction coefficient for newly released insulin. In order to download the updated insulin response coefficient, the user terminal 200 has to perform a process of paying certain usage fee.

The apparatus described herein may be implemented using hardware components, software components, and/or combination of the hardware components and the software components. For example, the apparatuses and the components described in the embodiments may be implemented using, for example, a processor, a controller, an arithmetic logic unit (ALU), a digital signal processor, a microcomputer, a field programmable gate array (FPGA), a programmable logic unit (PLU), a microprocessor, or one or more general-purpose computers or specific-purpose computers such as any other device capable of responding to and executing instructions in a defined manner. The processing device may run an operating system (OS) and one or more software applications that run on the OS. The processing device also may access, store, manipulate, process, and create data in response to execution of the software.

For convenience of comprehension, the description of a processing device is used as singular; however, one of ordinary skill in the art will be appreciated that a processing device may include multiple processing elements and/or multiple types of processing elements. For example, a processing device may include multiple processors or a processor and a controller. In addition, different processing configurations are possible, such as a parallel processor.

The software may include a computer program, a code, an instruction, or a combination of one or more thereof, for independently or collectively instructing or configuring the processing device to operate as desired. Software and/or data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed manner. The software and data may be stored by one or more computer readable recording media.

The method according to the embodiment of the disclosure may be recorded in non-transitory computer-readable media including program instructions to implement various operations embodied by a computer. The computer-readable media may also include, alone or in combination with the program commands, data files, data structures, etc. The media and program instructions may be those specially designed and constructed for the purposes, or they may be of the kind well-known and available to those of skilled in the computer software arts. Examples of computer-readable media include magnetic media such as hard disks, floppy disks, and magnetic tape; optical media such as CD ROM disks and DVD; magneto-optical media such as floptical disks; and hardware devices that are specially to store and perform program commands, such as read-only memory (ROM), random access memory (RAM), flash memory, etc. Examples of the program commands may include not only machine language codes but also high-level language codes which are executable by various computing means by using an interpreter. The aforementioned hardware devices may be configured to operate as one or more software modules to carry out exemplary embodiments, and vice versa.

While the present disclosure has been described with reference to exemplary embodiments, one of ordinary skill in the art may practice various changes and modifications without departing from the spirit and scope of the present disclosure set forth throughout the annexed claim matters. For example, there may be attained a desired result according to the present disclosure even though the techniques are carried out through other methods and procedures different from the aforementioned, and/or even though the system, the structure, the units and the circuits are coupled in other manners different from the aforementioned, or substituted or replaced with other components or equivalents.

Therefore, other implementations, other embodiments, and equivalents to the claims also fall within the scope of the following claims.

What is claimed is:

1. A method of managing a state of a patient after automatically injecting the patient with a medicine, the method comprising:

installing, by a user terminal for diabetes management, a drug injection program received from a management server thereon;

receiving, by the user terminal, at least one message selected from the group consisting of a drug injection message including usage data of a drug injection device, a biometric value measurement message, and a device state message, from a controller via the drug injection program;

receiving, by the user terminal, an input of a risk alarm setting information from a user and transmitting, by the user terminal, the risk alarm setting information to the controller;

receiving, by the user terminal, a first risk signal corresponding to the risk alarm setting information from the controller;

determining a suitability of a blood sugar value based on blood sugar measurement values before and after an insulin injection included in the biometric value measurement message, an insulin injection amount included in the drug injection message, and a reaction coefficient;

generating, by the user terminal, a second risk signal based on the suitability of the blood sugar value determined;

generating, by the user terminal, a risk alarm message according to the first risk signal and the second risk signal; and determining, by the user terminal, a manager according to the first risk signal and the second risk signal, the manager having a manager terminal, and transmitting, by the user terminal, the risk alarm message to the manager terminal or a risk management center.

2. The method of claim 1, wherein the risk alarm message includes location information and is implemented to cause an additional alarm to be generated at a preset time point.

3. The method of claim 1, further comprising:

receiving, by the user terminal, the device state message from the controller and transmitting, by the user terminal, the usage data of the drug injection device to the management server during a drug non-injection time period;

receiving, by the user terminal, a payment link of a usage fee corresponding to the usage data from the management server; and executing, by the user terminal, the drug injection program based on completion of a payment and approval of the usage fee via the payment link.

4. A user terminal for managing a state of a patient after automatically injecting the patient with a medicine, the user terminal configured for diabetes management and having a drug injection program installed thereon, the user terminal comprises:

a message receiving unit configured to receive at least one message selected from the group consisting of a drug injection message including usage data of a drug injection device, a biometric value measurement message, and a device state message, from a controller via the drug injection program;

an information registration unit configured to register risk alarm setting information;

a risk signal generation unit configured to;

determine, using at least one of the drug injection message, the biometric value measurement message, or the device state message, a risky situation;

receive, from the controller, a first risk signal corresponding to the risky situation and the risk alarm setting information;

determine a suitability of a blood sugar value based on blood sugar measurement values before and after an insulin injection included in the biometric value measurement message, an insulin injection amount included in the drug injection message, and a reaction coefficient; and generate a second risk signal based on the suitability of the blood sugar value determined; and a risk alarm generation unit configured to generate a risk alarm message according to the first risk signal and the second risk signal, determine a manager according to the first risk signal and the second risk signal, the manager having a manager terminal, and transmit the risk alarm message to the manager terminal or a risk management center.

5. The user terminal of claim 4, wherein the risk alarm message includes location information and is implemented to cause an additional alarm to be generated at a preset time point.

6. The user terminal of claim 4, wherein the risk alarm generation unit is further configured to, when the first risk signal is received, determine a recipient group for the risk alarm message according to a risk code of the risky situation and a risk type of the risky situation.

7. A computer-readable program stored in a non-transient computer-readable storage medium for executing the method according to claim 1 by using a computer.

* * * * *